(12) United States Patent
Dunn

(10) Patent No.: US 6,540,353 B1
(45) Date of Patent: Apr. 1, 2003

(54) CONTACT LENS AND PROCESS FOR FITTING

(75) Inventor: Stephen A. Dunn, Honolulu, HI (US)

(73) Assignee: Polyvue Technologies, Inc., Larkspur, CA (US)

( * ) Notice: Subject to any disclaimer, the term of this patent is extended or adjusted under 35 U.S.C. 154(b) by 0 days.

(21) Appl. No.: 09/212,904

(22) Filed: Dec. 16, 1998

Related U.S. Application Data

(63) Continuation of application No. 08/716,199, filed as application No. PCT/US96/15589 on Sep. 27, 1906, now Pat. No. 5,864,379.
(60) Provisional application No. 60/004,567, filed on Sep. 29, 1995.

(51) Int. Cl.[7] .............................. G02C 7/04; A61F 2/16; A61B 18/18
(52) U.S. Cl. ........................... 351/161; 623/6.24; 606/5
(58) Field of Search ........................... 351/161, 16 OR, 351/16 OH, 162, 168–169, 171; 623/6.24, 6.27–6.28; 606/4–6

(56) References Cited

U.S. PATENT DOCUMENTS

| | | | |
|---|---|---|---|
| 4,199,231 A | 4/1980 | Evans | 351/160 H |
| 4,340,283 A | 7/1982 | Cohen | 351/161 |
| 4,582,402 A | 4/1986 | Knapp | 351/162 |
| 4,636,049 A | 1/1987 | Blaker | 351/161 |
| 4,636,211 A | 1/1987 | Nielsen et al. | 6/6.28 |
| 4,668,240 A | 5/1987 | Loshaek | 8/507 |
| 4,704,016 A | 11/1987 | de Carle | 351/161 |
| 4,704,017 A | 11/1987 | Knapp | 351/177 |
| 4,813,955 A | 3/1989 | Achatz et al. | 623/6.17 |
| 4,869,587 A | 9/1989 | Breger | 351/161 |
| 4,950,057 A | 8/1990 | Shiravanagi | 351/169 |
| 4,976,534 A | 12/1990 | Miege et al. | 351/161 |
| 5,002,382 A | 3/1991 | Seidner | 351/161 |
| 5,139,325 A | 8/1992 | Oksman et al. | 351/161 |
| 5,158,572 A | 10/1992 | Nielsen | 351/161 |
| 5,166,712 A | 11/1992 | Portney | 351/161 |
| 5,270,744 A | 12/1993 | Portney | 351/161 |
| 5,404,183 A | 4/1995 | Seidner | 351/161 |
| 5,406,341 A | 4/1995 | Blum et al. | 351/160 R |
| 5,530,491 A | 6/1996 | Baude et al. | 351/161 |
| 5,574,518 A | 11/1996 | Mercure | 351/161 |
| 5,608,471 A | * 3/1997 | Miller | 351/161 |

FOREIGN PATENT DOCUMENTS

| | | |
|---|---|---|
| EP | 0 138 394 | 9/1983 |
| EP | 0 140 063 A1 | 9/1984 |
| EP | 0 201 231 | 11/1986 |
| JP | 2 217 818 | 8/1990 |
| JP | 5 181 096 | 7/1993 |
| WO | PCT/FI85/00103 | 7/1986 |

OTHER PUBLICATIONS

L. Bronstein, "Reverse Centrad Biofocal Contact Lenses", Optometric Weekly, vol. 59, No. 25, Jun. 20, 1968, pp. 45–48.

(List continued on next page.)

*Primary Examiner*—Jordan M. Schwartz
(74) *Attorney, Agent, or Firm*—George W. Neuner; Edwards & Angell, LLP

(57) ABSTRACT

An aspheric multifocal contact lens for wearing by a patient with presbyopia is disclosed. The lens has a lens body with a rear surface adapted to fit on the surface of the eye and a front surface that interacts with the rear surface to bring about the desired optics of the lens. The lens also has a centrally located and generally circular first optic zone providing a first power correction for near vision, and a second optic zone concentric with the first optic zone and located peripherally therefrom providing a second power correction for distance vision. A transition zone concentric with the first optic zone is located between said first and second optic zones. The transition zone provides a rapid power shift of about 0.8 to about 1.6 diopters over a distance of about 0.25 mm between the power correction of the first and second zones.

10 Claims, 2 Drawing Sheets

OTHER PUBLICATIONS

N. Bier, "Prescribing for Presbyopia With Contact Lenses", Opthalmic Optician, vol. 5, No. 9, May 1, 1965, pp. 439–442 and 447–454.

"Contacts for aging baby boomer's eyes?", Science News, vol. 150, Sep. 7, 1996, p. 159.

"The Cals Lens/Unilens", by Thomas C. Evans, Harvey B. Mayers and John M. Szabocsik, Optometry Today, Nov. 5, 1988.

"The Sunsoft Multifocal—A New Bifocal Contact Lens", an Overview by N. Rex Ghormley, ICLO, vol. 23, Mar./Apr., 1996.

"A Soft Approach to Presbyopia", by Craig W. Norman, F.C.L.S.A. & Ursula Lotzkat, Spectrum, Aug., 1995, pp. 27–31.

"Stressing Success with Your Presbyopic Contact Lens Patients", by Craig W. Norman, F.C.L.S.A. & Ursula Lotzkat, Spectrum, May, 1995, pp. 29–36.

"Strategies for Success with Presbyopes", by Neil A. Pence, O.D., F.A.A.O., Spectrum, May 1994, pp. 30–38.

* cited by examiner

CONTACT LENS AND PROCESS FOR FITTING

This application is a continuation of U.S. Ser. No. 08/716,199 (now U.S. Pat. No. 5,864,379) filed Sep. 27, 1996, which is a 371 application of PCT/US96/15589 filed Sep. 27, 1996, which claims priority of U.S. Ser. No. 60/004,567 filed Sep. 29, 1995.

TECHNICAL FIELD

This invention relates to a contact lens that restores the ability to focus on objects within a range of distances near to the user (referred to as "natural accommodation"), while retaining the ability to see distant objects. More specifically, this invention relates to a contact lens with a conventional spherical concave surface conforming to the curvature of the eye (base curve) and having a non-conventional convex surface (optic curve) combining spherical and non constant aspherical curvature resulting in an optical system that provides true monocular presbyopic correction (correction of presbyopia in each eye independently, instead of partial or full distance correction in one eye and partial or full near correction in the other) and restores the phenomenon of "natural accommodation." Additionally, the invention affords a methodology of fitting that substantially reduces the skill and experience required by the contact lens fitter to a very basic level while affording a high degree of clinical success and patient satisfaction.

Normally between the ages of 40 and 45, presbyopia or old sightlessness is brought about by loss of elasticity of the crystalline lens of the eye, causing blurred vision at near points due to the reduction of the ability of the eye's natural lens to accommodate the changes in curvature necessary to focus on both near and distant objects.

When a person is free of presbyopia, the eye retains its full range of natural accommodation. This type of person's vision can be corrected by eyeglasses or contact lenses providing only the correction required for distance vision, and natural accommodation would automatically provide correction for near and intermediate distance vision.

BACKGROUND ART

For the contact lens wearer who requires presbyopic (or near vision) correction, in addition to distance correction, a variety of options have been available. These individuals may be fitted with single vision contact lenses corrected for distance, and wear reading glasses for near correction. Another alternative is to provide a contact lens for one eye that is corrected for distance vision and to provide a contact lens for the other eye that is corrected for near vision (this practice is referred to as monovision because only one eye is corrected for near vision), or the fitting of bifocal or multifocal contact lenses.

During the 1950's, a variety of contact lenses were designed for the correction of presbyopia. Theme contact lenses, although very innovative in design, met with only limited success because the only readily available material was Poly Methyl Methacrylate (Plexiglass), also known as PMMA which does not transmit oxygen. As bifocal and multifocal designs of the period were quite thick and heavy compared to conventional distance correction contact lenses, these presbyopic contact lenses were uncomfortable to wear for substantial periods of time. Additionally, the fitting of these bifocal and multifocal contact lenses required considerable time and skill on the part of the contact lens fitter.

During the 1970's, both soft contact lenses and rigid gas permeable (RGP) contact lenses were introduced with the availability of these new materials, renewed enthusiasm brought about several new designs for contact lenses for the correction of presbyopia.

RGP materials provide oxygen transmission through the lens material itself, and afforded new hope for the earlier designs developed in PMMA material. However, lens thickness and resultant patient discomfort continued to be a problem.

One of the early benefits recognized with soft contact lenses was the comfort and ease of fitting and, for this reason, by 1995 approximately 85% of new contact lens wearers are being fitted with soft contact lenses. As soft contact lenses command such a large share of the contact lens market, it is natural that considerable effort would be made to develop bifocal and multifocal contact lens designs in soft contact lens material.

There are two types of contact lens designs for the correction of presbyopia—Alternating (or Translating) and Simultaneous.

(1) In the alternating (or translating) vision technique, the lenses are very similar in design to bifocal eyeglass lenses in that the wearer sees through the distance segment in the upper portion of the lens when looking straight ahead and sees through a lower near vision segment when the eye (moves) to look down. Alternating vision lenses have proven to be successful in RGP designs, but have met with little success when designed in soft contact lenses.

Perhaps the reason that alternating vision soft contact lens designs were not as successful as the same design concept in RGP materials was because lens translation is necessary for this design to be successful. The translation from distance to near is achieved through the mechanical action of the lens resting on the lower eyelid and, when the eye looks down, the lens remains stable on the lower eyelid causing the pupil of the eye to translate from the distant vision portion of the lens to the near vision portion of the lens. Soft lens material by its nature caused this modality to fail as there was insufficient rigidity in the soft lens to remain properly positioned on the lower eyelid and often the lens would slip underneath the lower eyelid during translation.

(2) Simultaneous vision bifocal or multifocal contact lenses are either concentric or aspheric in design with focal power changing through different areas of the lens. Lenses are fitted so that distance, intermediate and near zones focus images simultaneously on the retina of the eye and the brain then separates out the image desired.

Theoretically, with adaptation, the ability to change focus naturally from near to far with no blurring in between can be achieved with simultaneous vision lenses in both RGP and soft contact lenses.

As alternating presbyopic designs proved to be unsuccessful in soft contact lens designs, most of the development work with soft contact lenses was done in the area of simultaneous presbyopic correction with concentric designs or aspheric designs.

During the 1980's, several designs of concentric and aspheric soft contact lenses were introduced. Soft aspheric multifocal contact lenses typically provided relatively weak reading addition power and therefore worked beat in early presbyopia.

Reading addition powers are referred to by eye care professionals as "add" power, and represent the difference between the distance correction and near correction prescribed by an eye care professional for eyeglasses or contact lenses. Accordingly, a prescription of "−3 with a +2 add"

(which would be typical for moderate presbyopia) would mean that distance vision requires −3 diopters of correction, and near vision requires an additional 2 diopters of plus correction, resulting in −1 diopters of near vision correction. In conventional monovision, the dominant eye would be fitted with a −3 distance correction lens, and the other eye would be fitted with a −1 near correction lens.

This type of solution is often satisfactory in early presbyopia because the user still has some remaining visual accommodation and the needed add power is usually between +0.75 and +1.25, which is usually low enough for the brain to comfortably select the desired image in most people. However, conventional monovision becomes less satisfactory as, presbyopia becomes more advanced because the needed add power increases and visual accommodation has deteriorated further, so that the visual imbalance exceeds the brain's ability to select the desired image from the appropriate eye.

Typically, early presbyopes, would be between the age of 40 and 45, and would require add power of between +1.00 and +1.50 diopters. Moderate presbyopes would usually be between 45 and 55 years and would require add power of between +1.50 and +2.00 diopters. Mature presbyopes would usually be older than age 55 and require an add power of between +2.00 and +3.00 diopter.

The add corrective power of current aspheric multifocal contact lens designs is usually limited to only +0.75 to +1.25 diopters because the brain must be able to separate out the desired image (and also suppress the undesired images) from the multiple images (near, intermediate or distant) being simultaneously focused by the multifocal contact lens design. In order to achieve this suppression, the images cannot be too different from each other. However, if aspheric corrections are increased in attempts to achieve higher add powers, the images become too different for the brain to suppress the undesired images, resulting in blurred vision. Even at add powers of +0.75 to +1.25 diopters, many patients suffer some blurring or ghosting with multifocal contact lens designs because their brains are not able to completely separate the desired image while simultaneously completely suppressing the undesired images.

Some contact lens fitters may attempt to use aspheric designs to achieve near distance correction of up to +2.00 diopters (or more) by undercorrecting the distance vision of the non-dominant eye by between 0.25 and 1.00 diopters, thereby theoretically providing up to +2.00 diopters (or more) of near vision correction, instead of the +0.75 to +1.25 diopter correction that would be provided if that eye had been fully corrected for distance vision with an aspheric multifocal contact lens. The dominant eye would be corrected to maximum distance acuity in such a situation. However, this creates even more blurring and ghosting. This technique is called modified monovision.

Aspheric optics have been incorporated on both the front and back surfaces of soft contact lenses. However, it is believed that front surface aspherical multifocal soft contact lenses provide better presbyopic correction. Still, only limited success is achieved because providing add power of +0.75 to +1.25 (or more) usually results in reduced distance acuity. For this reason, many contact lens fitters find it necessary, when using aspheric soft multifocal contact lenses, to undercorrect the distance power in one eye to improve near vision, while correcting the other eye fully for distance vision, as discussed above. When attempting to fit moderate to mature presbyopes, this modified monovision almost always results in a visual compromise similar to that of conventional monovision.

Concentric multifocal lens designs have an advantage over aspheric designs in the fitting and correcting of more mature presbyopes requiring add power of more than +1.25 diopters, primarily due to the availability of higher add power correction and central power zones of different diameters. Concentric soft multifocal contact lenses have been made with the central distant correction zones and central near correction zones in the latter designs, the central power zones would be corrected by the amount prescribed to correct near vision. It is believed that central near add zones have been more successful at correcting presbyopia than central distance zones, when incorporated in concentric multifocal soft lens designs. Although concentric center add multifocal designs have the ability to correct higher add power requirements, most individuals fitted with this type of lens experience moderate to significant amounts of visual discomfort due to ghosting of images or a 3-D effect, at near distances. These effects diminish with adaptation, but still cause a high portion of wearers to discontinue the use of this type of presbyopic contact lens.

The reality of the existing art of presbyopic correction with simultaneous vision contact lenses is that no currently available lens system, be it aspheric or concentric, provides monocular multifocal correction for moderate to mature presbyopia. In most cases, some form of modified monovision is required in an attempt to satisfy the visual requirement for near and far vision. To this end almost all currently available presbyopic contact lens manufacturers indicate in their fitting manuals the requirement of compensating one eye more for near and the other eye more for distance correction. This is the norm rather than the exception. Additionally, no currently available multifocal contact lens has the ability to restore the phenomena of natural accommodation and successful results are difficult to achieve and require considerable time and experience on the part of the fitter.

It is therefore an object of this invention to provide true multifocal correction for moderate and mature presbyopes requiring up to +3.00 diopters of add power without the need to compensate one eye for near and the other eye for distance.

It is a further object of this invention to provide rapid patient adaptation with minimal initial visual discomfort.

It is a still further object of this invention to provide a presbyopic optical system that restores the phenomenon of natural accommodation.

It is a still further object of this invention to provide a system of fitting and methodology that allows a contact lens fitter with little or no multifocal contact lens fitting experience to achieve a very high degree of success and patient satisfaction.

Disclosure of Invention

These and other objects are achieved by a contact lens having a central circular region (an "accommodation zone" or "sweet spot" named zone 1) that in overcorrected for near vision, and that is small enough that it does not impair distance vision. Preferably, a plurality of concentric transition region (or rings), optimally two (named zone 2 and zone 3, progressing radially outwardly), are provided between the sweet spot and the outer region (or ring) of the lens (named zone 4), which 8 corrected for distance vision. Preferably, the sweet spot has a diameter of between approximately 1.0 millimeters and approximately 2.5 millimeters, preferably between approximately 1.5 millimeters and approximately 1.9 millimeters, and optimally either approximately 1.5 millimeters or approximately 1.9 millimeters, Preferably, the transition rings (zones 2 and 3) are each approximately 0.5 millimeters wide. Preferably also, the remaining portion of the lens (zone 4) extends radially outward from the outermost transition ring to at least approximately 8 millimeters. Because the human pupil cannot expand beyond approximately 8 millimeters in diameter, the portion of the lens extending more than approximately 8 millimeters radially outward from the center is not an optical portion and functions only as a carrier.

Preferably, the sweet spot is spherical and is overcorrected by between 25% and 100% over the near vision correction prescribed for the user. Preferably, the remaining optical portions of the lens are aspheric, with different diopter shifts over different regions. Optimally, for high add power, zone 2 provides a diopter shift of approximately 1.6 diopters, zone 3 provides a diopter shift of approximately 1.2 diopters, and zone 4 provides a diopter shift of approximately 0.9 diopters. For low add power, optimally zone 2 provides a diopter shift of approximately 0.1.1 diopters, zone 3 provides a diopter shift of approximately 0.8 diopters, and zone 4 provides a diopter shift of approximately 0.6 diopters.

The contact lens manufacturing lathe disclosed in the example below provided contact lenses that achieved the desired results. However, some experimentation may be necessary to achieve the desired result with different equipment, but this experimentation should not be undue.

The invention incorporates both concentric and aspheric design principles and can be produced with a high add power correction or a low add power correction. In addition, the lens system offers two accommodation zone diameters for different sized pupils to achieve maximum near point acuity without reduction in distance visual acuity.

The higher add power lens has a power transition of 3.7 diopters across the usable optic zone, and the low add power lens has a power transition of 2.6 diopters across the usable optic zone.

The accommodation zone should cover approximately 50% of the pupil area for maximum success in distant, intermediate and near visual acuity. The accommodation zone functions to restore the phenomenon of natural accommodation by creating a very small area of over magnification in the center of the pupil of approximately 25% to 100% over the near vision correction required by the indicated reading add power. Surprisingly, distance vision will not be substantially impaired if the accommodation zone covers 50% or less of the pupil area. Further, the function of natural accommodation will be restored to an unexpectedly great extent.

Although the inventor is not sure (and the validity and enforceability of any patent issuing hereon shall not be affected by the accuracy or inaccuracy of this explanation), the inventor believes that, in near vision, a user's pupils constrict, so that the accommodation zone occupies a largo enough portion of the pupil area for the accommodation zone to become effective. Normal reading correction is prescribed for approximately 15 inches (approximately 38 centimeters). Accordingly, the overcorrection of the accommodation zone (sweet spot) allows the user to ace from 8 inches to 15 inches, thus restoring the function of natural accommodation. In distance vision, however, the pupil will be normally dilated, so that the accommodation zone is small enough that the brain ignores the image generated by it. The constriction of the pupil for near vision is known as "accommodative pupil response."

The accommodation zone is blended to the distance zone 4 via two zones of non constant aspherocity which allows true monocular correction of near, intermediate and distant vision. Near vision correction, when tested at the standard distance of approximately 15 inches (approximately 38 centimeters) offers normal best corrected acuity and when reading material is brought closer to the eyes, up to about eight inches (approximately 20 centimeters), near acuity remains stable and often improves due to the increased near power created by the sweet spot.

Due to the non constant aspheric transition from the sweet spot to zone 4, adaptation problems associated with prior designs of concentric or aspheric multifocal contact lenses are substantially reduced or eliminated completely.

Historically, the fitting of multifocal contact lenses has been more an art than a science as the variables associated with fitting presbyopic contact lenses are considerable. Often success has only been achieved through the process of trying many different lenses on the patient in the hope of finding a lens that generates a good presbyopic response. The contact lens fitter's degree of experience in the fitting of multifocal lenses has also been a key to achieving a successful fitting with good visual results.

The fitting of lenses according to this invention requires accurate centering of the lens over the pupil of the eye in order to achieve the expected results. To determine the location of the sweet spot relative to the pupil is often difficult because the pupil may not be aligned with the center of the cornea or for other reasons. Thus, the invention also incorporates the use of a diagnostic trial lens with a white ring corresponding in diameter and location to the sweet spot. The exact position of the center of the contact lens can be determined and the relative position of the sweet spot to the pupil and the percentage of pupil covered by the sweet spot is easily observed. The use of the diagnostic lens allows the fitter to very quickly determine the proper sweet spot size, which increases the chances of successful fitting. For example, if the accommodation zone does not align within the pupil, the fitter knows that the standard lens design will not work and a custom lens design with an offset accommodation zone will be required.

Other objects, features and advantages of the present invention will become more fully apparent from the following detailed description of the presently preferred embodiments for carrying out the invention and the accompanying drawings.

BEST MODES FOR CARRYING OUT INVENTION

The presently preferred best modem for carrying out the present invention are illustrated by way of example in FIGS. 1 to 4.

Figure 1:
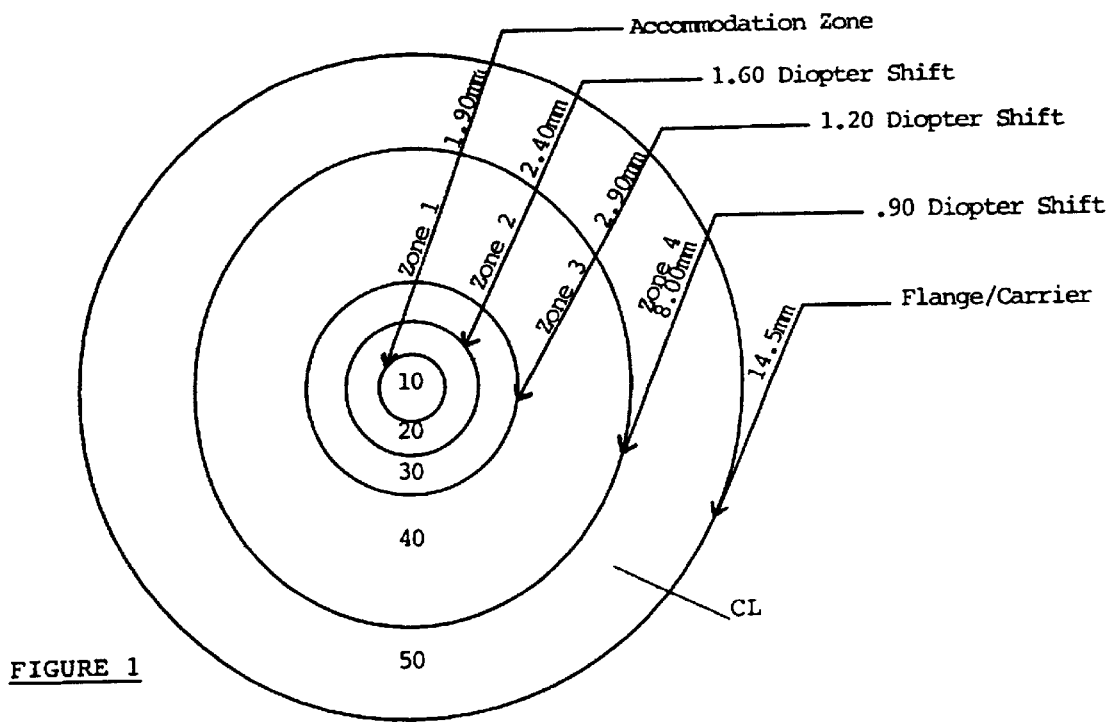
FIG. 1 is a top elevational schematic view of a presently preferred embodiment of a contact lens according to the present invention for a person who needs a high degree of reading correction (high add power) and a larger sweet spot.

Referring to FIG. 1, shown is a first preferred embodiment of a contact lens CL according to the present invention. The contact lens CL is divided into a central circular region and four concentric ring shaped regions. The central region 10 will be referred to as tone 1, the accommodation zone, or the sweet spot. The immediately adjacent first ring shaped region 20 will be referred to as zones 2. The second ring shaped region 30 immediately adjacent to zone 2 will be referred to as zone 3. The third ring shaped region 40 immediately adjacent to zone 3 will be referred to as zone 4.

The maximum diameter of a human pupil when it is fully dilated is approximately 8 millimeters, so that the ring shaped region 50 of the contact lens extending radially outwardly from zone 4 is not an optical surface, but merely functions as a carrier to maintain the optical surface of zones 1 through 4 in position.

Structurally, the zones can be described as follows. Zone 1 is preferably approximately 1.5 to 1.9 millimeters in diameter. Zone 2 and zone 3 are both preferably approximately 0.5 millimeters in width. Zone 4 preferably extends outwardly from a radius of approximately 2.5 millimeters to approximately 2.9 millimeters to approximately 8 millimeters. Thus, the lens can be described as having a central sweet spot (zone 1), two 0.5 millimeter intermediate zones (zones 2 and 3), and a distance zone (zone 4) extending outwardly from the intermediate zones to the edge of the optical portion of the contact lens (approximately 8 millimeters radially outwards from the center). The total diameter of the contact lens CL will be approximately 13 to approximately 16 millimeters for a soft contact lens, so that the carrier 50 will normally extend from approximately 8 millimeters outwards to approximately 13.5 millimeters to approximately 15.0 millimeters, and optimally 14.5 millimeters.

If this invention is practiced in connection with a hard contact or RGP lens, the total diameter of the contact lens CL would be between approximately 7.0 millimeters and approximately 11.0 millimeters, and typically between approximately 8.0 millimeters and approximately 10.5 millimeters, and optimally approximately 9.5 millimeters.

Zone 1, the sweet spot, is preferably spherical, although it can be aspherical. Zones 2, 3 and 4 are preferably aspherical in order to accommodate transitions in corrective power across these zones.

Conventional contact lenses consist of a carrier with a central lens portion. The central lens portion 1i usually corrected for distance vision. This is described in U.S. Pat. No. 4,119,2312, Evans, which is hereby incorporated by reference.

The present invention differs from conventional multifocal contact lenses in that a small central portion of the lens is overcorrected beyond the correction that would be necessary for reading. This central portion, the sweet spot or accommodation zone, is small enough so that, surprisingly, it does not impair distance vision when the user is looking at distant objects, but it restores the ability to focus on near objects within a substantial range of distances from the wearer, such as, between 8 inches and 15 inches. It is believed that the transition zones restore the ability to focus as follows: zone 2 restores the intermediate visual acuity between approximately 15 inches and approximately 36 inches, and zone 3 restores the intermediate visual acuity between approximately 36 inches and full distance correction (infinity).

In determining the appropriate curvatures for the various zones in the contact lens CL, the correction to restore distance vision must be determined first. The distance power correction is then applied to zone 4. The distance power correction is usually within a range between +20.00 diopters to −20.00 diopters.

After the distance correction is determined, the amount of correction for near vision ("add power") should be calculated. A person with early to moderate presbyopia would be prescribed a low additional reading power of up to +1.75 diopters (referred to as a "low add"). A moderate to advanced presbyope would require a reading correction from 1.75 to 2.75 diopters (referred to as a "high add").

For a high add presbyope, the aggregate change in powers across the various zones is preferably approximately 3.7 diopters. For a low add presbyope, the aggregate change in powers across the various zones is preferably approximately 2.6 diopters (approximately 70% of the total diopter shift for a high add).

The corrective power of the various zones preferably does not remain constant within each zone. Instead, for a high add presbyope, it is preferred that there be as 1.6 diopter shift across zone 2, a 1.2 diopter shift across zone 3 and a 0.9 diopter shift across zone 4, so that the total diopter shift across zones 2, 3, and 4 is 3.7 diopters.

Because the sweet spot is so small, and because it must be centered in the pupil in order for the invention to function properly, the contact lens CL must be precisely manufactured in order to be sure the sweet spot is properly centered over the center of the pupil. In order to accomplish this critical centering, it is preferred to mark a 1.9 millimeter centered spot, preferably white, on a pair of trial diagnostic contact lenses with such a pair of trial diagnostic contact lenses, it is possible to detect whether a user's pupil is off center (and other problems), so that the contact lens of the present invention can be properly manufactured to center the sweet spot over the pupil.

The inventor has discovered that an overcorrected central portion of between approximately 1 to approximately 2.5 millimeters, and preferably approximately 1.5 to approximately 1.9 millimeters (optimally either 1.5 millimeters or 1.9 millimeters) in diameter does not substantially impair distance vision of a contact lens. Surprisingly, the inventor also has discovered that overcorrecting the central portion beyond the correction needed for near vision, restores an unexpectedly large portion of the function of natural accommodation of the eye so that focus can be achieved over a range of near distances.

Although, other contact lenses are known with central areas that are differently corrected than distance portions, those central segments are either larger than the present invention's "sweet spot," or they do not overcorrect the sweet spot, or both.

Figure 2:
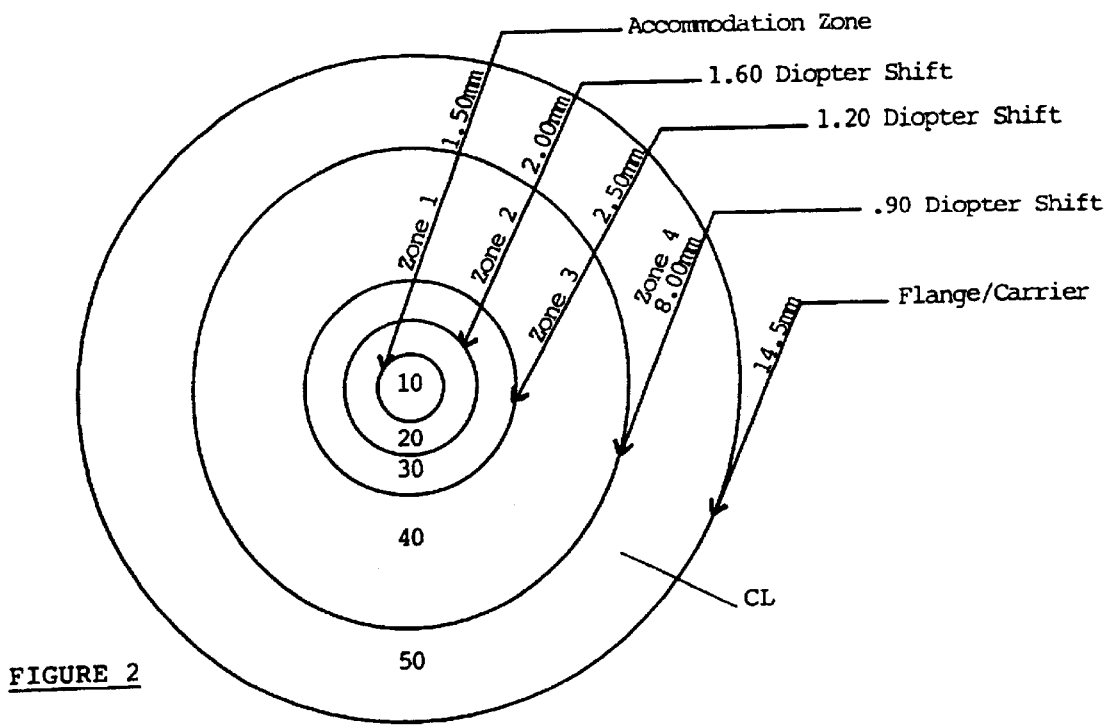
FIG. 2 is a top elevational schematic view of a presently preferred embodiment of a contact lens according to the present invention for a person who needs a high degree of reading correction (high add power) but a smaller sweet spot.

It is preferred that the various zones have constant widths even if the size of the sweet spot differs. Thus, if the sweet spot is 1.9 millimeters in diameter, the diameters of zones 2, 3, and 4 would all be approximately 0.4 millimeters greater than the corresponding diameters in a lens with a 1.5 millimeter diameter sweet spot. It is also preferred that the diopter shifts between zones 2, 3, and 4 remain constant regardless of the size of the sweet spot for mature presbyopes. FIG. 2 shows a contact lens according to the present invention with a smaller sweet spot.

Figure 3:
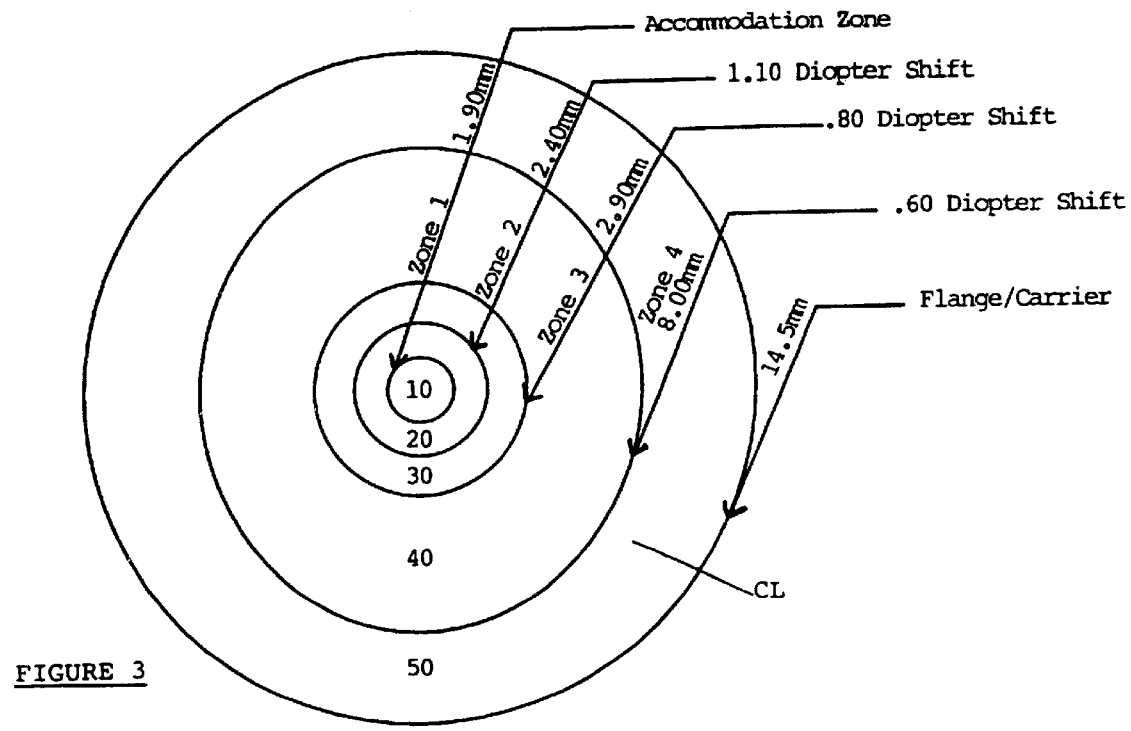
FIG. 3 is a top elevational view of a contact lens according to the present invention for a person who needs a lesser degree of reading correction (low add power) and a larger sweet spot.
Figure 4:
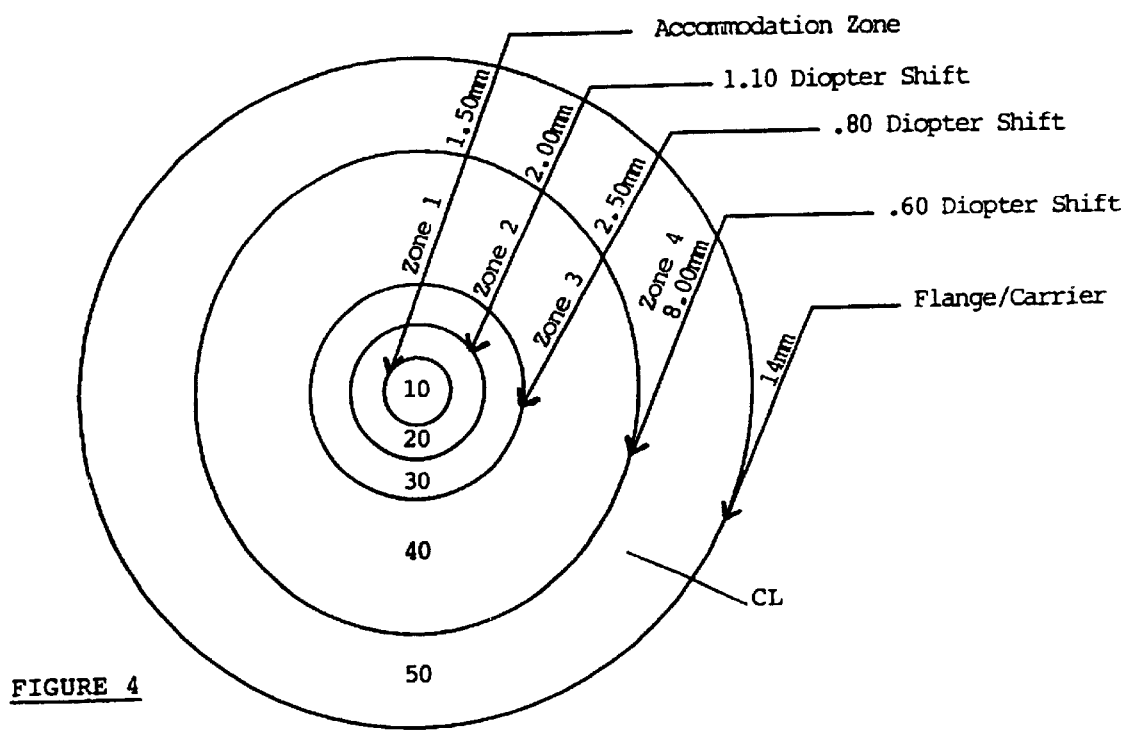
FIG. 4 is a top elevational view of a contact lens according to the present invention for a person who needs a lesser degree of reading correction (low add power) and a smaller sweet spot.

For early presbyopia, the amounts of the diopter shifts across zones 2, 3, and 4 are preferably approximately 70% of the diopter shifts for mature presbyopes. Thus, the preferred aggregate diopter shift for early presbyopes is approximately 70% of the diopter shifts for mature presbyopes. Thus, the aggregate diopter shift across zones 2, 3, and 4 would be approximately 2.6 diopters; the diopter shift across zone 2 will be approximately 1.1 diopters; the diopter shift across zone 3 would be approximately 0.8 diopters and the diopter shift across zone 4 would be approximately 0.6 diopters. FIGS. 3 and 4 show contact lenses for early presbyopes with large and small sweet spots.

Although It is presently preferred to have intermediate zone 2 and 3, it is not known whether the presence of such zones is critical to the invention. Further, it is not known whether the manner in which the diopter shift is achieved by the aspheric shape of the various zones is critical. At present, it is preferred that the diopter shift take place at a constant radial rate in each zone, so that there is a different constant diopter shift rate in each of zones 2, 3, and 4. However, it is also possible that the benefits of this invention may be achievable by using varying diopter shift rates within a zone, or to increase or decrease the number of zones.

Further, it is not believed to be critical that the diopter shifts be effected by shaping the contact lens. For example, it is possible to achieve the diopter shift by using material with differing indices of refraction in various different portions of the lens. Indeed, with appropriate control over the diffusion of materials with different indices of refraction during molding of contact lenses, it is possible that the present invention could be practiced with a lens that is spherical or that does not have differently formed lens portions.

The sweet spot is preferably overcorrected between 25% and approximately 100% stronger than the prescribed reading correction requirement.

For example, for a high add, it would be preferred that the sweet spot be from 3.5 to 5 diopters more plus add power than the distance zone (zone 4), between 3.5 to approximately 3.9 diopters being even more preferred, and approximately 3.7 diopters being optimal. For a low add, it would be preferred that the sweet spot be from 2.0 to 3.5 diopters more plus add power than the distance zone (zone 4), with between approximately 2.4 and approximately 2.8 diopters being more preferred, and optimally approximately 2.6 diopters.

EXAMPLE 1

A Microturn 9000 three axis radius lathe with aspheric surface cutting capabilities has been used to make contact lenses according to the present invention with base curves of 8.6 millimeters wet (6.6 millimeters dry). The lenses were manufactured dry from Ocufilcon B (a 53% water content material) and were hydrated afterwards. Therefore compensating calculations were made to achieve the appropriate hydrated parameters, such an base curve, radial expansion, linear expansion, power changes due to changes in index of refraction caused by hydration. When hydrating Ocufilcon B, the linear expansion parameter is approximately 1.35, the radial expansion parameter is approximately 1.30, and the power change parameter is approximately 0.57. The settings for the various radii of curvature in the various zones (for dry manufacturing using Ocufilcon B) are shown in the following cutting charts:

8.60 High Add Minus Power

| | Zone 1 | 2 | 3 | 4 | | | |
|---|---|---|---|---|---|---|---|
| CENTER | 1.10 | 1.50 | 1.90 | 6.00 | DIA. | C.T. | DIST. |
| POWER | 1.40 | 1.80 | 2.20 | 6.00 | DIA. | C.T. | POWER |
| p1 | 6.73 | 6.98 | 7.17 | 7.30 | | .16 | |
| −.25 | 6.77 | 7.02 | 7.21 | 7.35 | | .16 | |
| −.50 | 6.83 | 7.06 | 7.25 | 7.40 | | .16 | |
| −.75 | 5.86 | 7.11 | 7.29 | 7.46 | | .16 | |
| −1.00 | 6.90 | 7.15 | 7.33 | 7.50 | | .16 | |
| −1.25 | 6.93 | 7.18 | 7.37 | 7.53 | | .16 | |
| −1.50 | 6.96 | 7.22 | 7.41 | 7.58 | | .16 | |
| −1.75 | 7.00 | 7.25 | 7.45 | 7.62 | | .16 | |
| −2.00 | 7.05 | 7.29 | 7.49 | 7.66 | | .15 | |
| −2.25 | 7.09 | 7.33 | 7.53 | 7.70 | | .15 | |
| −2.50 | 7.13 | 7.37 | 7.58 | 7.75 | | .15 | |
| −2.75 | 7.17 | 7.41 | 4.62 | 7.79 | | .15 | |
| p1 | 6.73 | 6.93 | 7.06 | 7.17 | | .16 | |
| +.25 | 6.70 | 6.89 | 7.02 | 7.13 | | .17 | |
| +.50 | 6.67 | 6.85 | 6.98 | 7.10 | | .17 | |
| +.75 | 6.63 | 6.82 | 6.93 | 7.06 | | .17 | |
| +1.00 | 6.60 | 6.79 | 6.89 | 7.02 | | .17 | |
| −1.25 | 6.58 | 6.74 | 6.86 | 6.98 | | .17 | |
| +1.50 | 6.56 | 6.70 | 6.84 | 6.95 | | .17 | |
| +1.75 | 6.52 | 6.67 | 6.80 | 6.91 | | .17 | |
| +2.00 | 6.49 | 6.64 | 6.77 | 6.87 | | .18 | |
| +2.25 | 6.46 | 6.61 | 6.73 | 6.83 | | .18 | |
| +2.50 | 6.43 | 6.58 | 6.70 | 6.79 | | .18 | |
| +2.75 | 6.40 | 6.55 | 6.66 | 6.75 | | .18 | |
| +3.00 | 6.37 | 6.52 | 6.63 | 6.72 | | .19 | |
| +3.25 | 6.34 | 6.48 | 6.60 | 6.68 | | .19 | |
| +3.50 | 6.31 | 6.45 | 6.57 | 6.65 | | .20 | |
| +3.75 | 6.28 | 6.42 | 6.54 | 6.62 | | .20 | |
| +4.00 | 6.26 | 6.39 | 6.51 | 6.59 | | .20 | |
| +4.25 | 6.23 | 6.36 | 6.47 | 6.56 | | .20 | |

8.60 Low Add Minus Power

| | Zone 1 | 2 | 3 | 4 | | | |
|---|---|---|---|---|---|---|---|
| CENTER | 1.10 | 1.50 | 1.90 | 6.00 | DIA. | C.T. | DIST |
| POWER | 1.40 | 1.80 | 2.20 | 6.00 | DIA. | C.T. | POWER |
| p1 | 6.73 | 6.93 | 7.06 | 7.17 | | .16 | |
| −.25 | 6.77 | 6.96 | 7.10 | 7.21 | | .16 | |
| −.50 | 6.81 | 7.00 | 7.14 | 7.25 | | .16 | |
| −.75 | 6.85 | 7.03 | 7.18 | 7.29 | | .16 | |
| −1.00 | 6.89 | 7.07 | 7.22 | 7.33 | | .16 | |
| −1.25 | 6.93 | 7.11 | 7.25 | 7.37 | | .16 | |
| −1.50 | 6.97 | 7.15 | 7.29 | 7.41 | | .16 | |
| −1.75 | 7.01 | 7.19 | 7.33 | 7.45 | | .16 | |
| −2.00 | 7.05 | 7.24 | 7.37 | 7.50 | | .15 | |
| −2.25 | 7.08 | 7.28 | 7.41 | 7.54 | | .15 | |
| −2.50 | 7.12 | 7.32 | 7.46 | 7.58 | | .15 | |
| −2.75 | 7.16 | 7.36 | 7.51 | 7.62 | | .15 | |
| −3.00 | 7.20 | 7.40 | 7.55 | 7.67 | | .14 | |
| −3.25 | 7.23 | 7.44 | 7.59 | 7.71 | | .14 | |
| −3.50 | 7.27 | 7.48 | 7.64 | 7.76 | | .14 | |
| −3.75 | 7.31 | 7.52 | 7.68 | 7.80 | | .14 | |
| −4.00 | 7.35 | 7.57 | 7.73 | 7.85 | | .13 | |
| −4.25 | 7.39 | 7.61 | 7.77 | 7.89 | | .13 | |

It is preferred that the contact lenses conform to industry standards for inside radii, which for soft contact lenses are presently between 7.5 and 9.5 millimeters, and typically between 8.30 millimeters and 8.6 millimeters. For RGP and hard lenses, the industry standard inside radii are between 7.0 millimeters and 8.5 millimeters, and typically between 7.3 and 8.2 millimeters.

It is presently preferred that the contact lens of the present invention comprise conventional soft contact lens material, such as Ocufilcon B with 53% water content, because contact lenses have been successfully manufactured using this material. However, any conventional soft or rigid contact lens material may be used to practice the invention (as long as appropriate compensations are made for parameters that may change during hydration for soft contact lens material). The inventor believes that Benz 55G or Methafilcon A may be as good as, or better than, Ocufilcon B in the practice of the present invention, but no lenses according to the present invention have yet been made with these materials.

While the present invention has been disclosed in connection with the presently preferred embodiments described herein, it should be understood that there may be other embodiments which fall within the spirit and scope of the invention as defined by the claims. For example, this invention can be practiced with contact lenses that are made by any method now known or hereafter invented, including (but not limited to) molding, spin casting, or extruding. This invention also can be applied to intraocular lens Implants and refractive surgical procedures (including radial keratotomy, photo refractive keratotomy, and corneal implantation) that reshape the cornea. Furthermore, this invention can be practiced in combination with spherical or astigmatic (toric) contact lenses. Toric lens prescriptions comprise spherical power corrections, usually between +20 and −20 diopters (commonly between +8 and −8 diopters), and cylindrical power corrections, usually between 0.5 diopters and 10 diopters (commonly between 1 and 4 diopters). The present invention can be practiced within this entire range of toric (astigmatic) lens prescriptions. Accordingly, no limitations are to be implied or inferred in this invention except as specifically and explicitly net forth in the claims.

Industrial Applicability

This invention can be used whenever it is a desired to provide a contact lens that corrects for distance vision as well as near and intermediate vision.

What is claimed is:

1. An aspheric multifocal contact lens for wearing by a patient with presbyopia comprising a lens body having a rear surface adapted to fit on the surface of the eye and a front surface that interacts with the rear surface to bring about the desired optics of said lens;

said lens having a centrally located and generally circular first optic zone providing a first power correction for near vision, and a second optic zone concentric with the first optic zone and located peripherally therefrom providing a second power correction for distance vision;

said improvement comprising a transition zone concentric with the first optic zone and located between said first and second optic zones, said transition zone providing a rapid power shift over a distance between the power correction of said first and second zones, wherein said rapid power shift is a power shift of about 0.8 to about 1.6 diopters over a distance of about 0.25 mm.

2. A lens according to claim 1 wherein the transition zone provides for a power shift of about 1.1 to about 1.6 diopters over a distance of about 0.25 mm.

3. An aspheric multifocal contact lens for wearing by a patient with presbyopia comprising a lens body having a rear surface adapted to fit on the surface of the eye and having at least two concentric optic zones:

a centrally located first optic zone having an add power range of from about 1.75 to 2.75 diopters;

a second optic zone having a power correction for distance vision; and a transition zone between said optic zones providing for a power shift over a distance of about 0.25 mm and having an add power range of from about 1.1 to 1.6 diopters.

4. An aspheric multifocal lens for use in correcting presbyopia in a patient which is generally circular in shape and comprises:

(i) a central optic zone having a first power correction range, (ii) at least one additional optic zone located peripheral of and concentric to said first zone and having an additional power correcting range, and (iii) a transition zone located between each of the optic zones having power correcting ranges to provide a rapid power shift of about 1.1 to 1.6 diopters over a lens surface distance of about 0.25 mm.

5. A lens according to claim 4 wherein the central optic zone has a power range for near vision correction.

6. A lens according to claim 5 which has one additional optic zone that has a power range for distance vision correction.

7. A lens according to claim 6 which is a contact lens.

8. A lens according to claim 6 which is a intraocular lens.

9. An aspheric multifocal contact lens for wearing by a patient with presbyopia comprising a transparent lens body having a rear surface adapted to fit on the surface of the eye and a front surface which interacts with the rear surface to provide the desired optics:

a centrally located and generally circular first optic zone providing a first range of power correction for near vision;

a second optic zone concentric with the first optic zone and located peripherally therefrom providing a second range of power correction for distance vision; and a transition zone located between said first and second optic zones and providing a rapid power shift between the power correction of said first and second zones over a transition zone distance of about 0.25 mm, wherein said rapid power shift is a power shift of about 0.8 to about 1.6 diopters over a distance of about 0.25 mm.

10. A refractive surgical procedure, comprising:

shaping a human cornea to provide:

a circular central region overcorrected for near vision, wherein said central region is small enough to avoid impairing distance vision;

at least one ring shaped transition region extending radially outward from said central region;

a ring shaped outer region extending radially outward from said transition region corrected for distance vision;

wherein said transition region provides at least a partial diopter shift over said transition region between said overcorrection of said central region and said distance correction of said outer region.

* * * * *